United States Patent
Polaschegg

(12) 
(10) Patent No.: US 6,623,443 B1
(45) Date of Patent: Sep. 23, 2003

(54) METHOD AND DEVICE FOR THE DETECTION OF STENOSIS IN EXTRA-CORPOREAL BLOOD TREATMENT

(76) Inventor: Hans-Dietrich Polaschegg, Oberdorf 92, A-9231, Koestenberg (AT)

( * ) Notice: Subject to any disclaimer, the term of this patent is extended or adjusted under 35 U.S.C. 154(b) by 0 days.

(21) Appl. No.: 09/477,198

(22) Filed: Jan. 4, 2000

(30) Foreign Application Priority Data

Jan. 14, 1999 (DE) ......................... 199 01 078

(51) Int. Cl.[7] .................. A61M 37/00; B01D 61/24; C02F 1/00
(52) U.S. Cl. .............. 604/5.04; 604/6.09; 604/4.01; 210/646; 210/741
(58) Field of Search ............... 210/645, 646, 210/739, 741, 745, 746, 767, 781, 782; 604/65–67, 505, 507, 6.16, 5.01, 5.04, 6.06, 6.09

(56) References Cited

U.S. PATENT DOCUMENTS

| | | | | |
|---|---|---|---|---|
| 4,873,989 A | * | 10/1989 | Einzig ..................... 356/478 |
| 5,484,397 A | * | 1/1996 | Twardowski ................ 210/636 |
| 6,077,443 A | * | 6/2000 | Goldau ..................... 210/143 |
| 6,193,669 B1 | * | 2/2001 | Degany et al. ............. 600/486 |
| 6,200,485 B1 | * | 3/2001 | Kitaevich et al. ........... 210/645 |

* cited by examiner

*Primary Examiner*—Angela D. Sykes
*Assistant Examiner*—Leslie R. Deak
(74) *Attorney, Agent, or Firm*—Frederick C. Williams; Trevor D. Arnold; Yan Lan

(57) ABSTRACT

Stenosis in a blood access circuit (graft, fistula) or in an extracorporeal circuit are detected by monitoring pressure pulses in the extracorporeal circuit created either by the heart or by the peristaltic blood pump of the extracorporeal circuit. By monitoring pressure pulses created by the. peristaltic blood pump loss of occlusion of the blood pump can be detected. Measurement of the pressure pulses is done either with sensors already built into the blood treatment equipment or, according to the invention, with sensors mechanically coupled to the wall of the blood tubing. The deviation of a pressure pulse amplitude proportional signal from a predetermined value indicates stenosis or loss of occlusion, respectively.

26 Claims, 6 Drawing Sheets

METHOD AND DEVICE FOR THE DETECTION OF STENOSIS IN EXTRA-CORPOREAL BLOOD TREATMENT

The invention concerns a method for the detection of stenosis in the blood circuit for extracorporeal blood treatment. The stenosis can be in the systemic blood circuit of the patient as well as in the extracorporeal blood circuit. The method evaluates pressure pulses produced either by the heart or by the blood pump of the extracorporeal circuit.

In one embodiment of the invention the pressure pulses in the extracorporeal circuit are measured non-invasively and without use of special pressure transducer membranes but directly on the tubing. The invention is explained more closely in the following description and in the patent claims.

Extracorporeal blood treatment today is a standard method, used especially for the treatment of end stage renal disease in the form of hemodialysis, hemodiafiltration or hemofiltration, but also employed for the treatment of hypercholesterinemia and for auto-immune diseases. Other extracorporeal treatment methods are based of physical effects, e.g., irradiation of blood with light, UV light or high-energy radiation (e.g., x-ray, beta- or gamma radiation). Furthermore, the application of increased or reduced temperature, and of magnetic, electric or electromagnetic fields is known.

For the extracorporeal treatment, a sufficiently effective access to the blood circuit of the body is required. For chronic treatment this access must remain patent for many years. The improvement of the treatment has resulted in many long-term patients. In addition the treatment of elderly patients became possible. Both are the causes that blood access becomes a growing problem and that it is often called the "achilles heel" of hemodialysis. The standard for blood access is a subcutaneous shunt between an artery and a vein. This shunt is created either by the connection of two blood vessels (Cimino-fistula) or with the help of an artificial vessel (graft). Blood accesses of this kind and the surgical techniques for their creation are described in all standard books on hemodialysis.

Some common problems with these blood accesses are stenosis, which are strictures of the vessels that may result in the total closure of the vessel and the loss of the fistula or graft if they are not detected and corrected timely. The word fistula will be used in the following for simplicity but the description is valid for grafts too.

The blood flow in a functional fistula is typically 700 ml/min with a wide range of 300–1500 ml/min. Larger blood flows have been measured too but there is a tendency to correct such blood accesses because high blood flow causes strain of the heart. In the extracorporeal circuit blood is commonly pumped with 200–500 ml/min. A blood flow in the fistula less than the blood flow in the extracorporeal circuit results in recirculation and therefore in a reduction of the efficacy of the method. It has been found that stenosis resulting in a blood flow of less than 600 ml/min in grafts will be followed by a total closure within short time. Early detection of this situation allows correction of stenosis before the total closure results in a total loss of the access. Because 600 mL/min are more than the commonly used flow in the extracorporeal circuit, it is not possible to detect this by a simple recirculation measurement. The fistula flow is therefore measured from time to time in order to detect stenosis timely. This is possible, e.g., with an ultraosound-doppler method requiring an expensive device and specialists. Such devices and knowledge are normally not available in dialysis units. An alternative method has been developed that measures recirculation with reversed blood flow in the extracorporeal circuit. Recirculation is then measured with a common method and the fistula flow is calculated. This method too requires a special device and trained personnel. Although it can be done in the dialysis unit it has not been adopted widely because it always requires an interruption of the treatment and is not cost effective therefore. This method is described in the U.S. Pat. No. 5,685,989.

Furthermore it has been recognized that the pressure measured in the extracorporeal circuit is influenced by stenosis in the fistula. Methods have been developed allowing detection of stenosis under certain circumstances. One method takes advantage of the empirical finding that information about stenosis downstream of the fistula can be gained from the venous pressure measured in the extracorporeal circuit provided a specific blood flow and specific cannulas are used. Stenosis is assumed when the venous pressure is above a limit evaluated by the clinic before. A description of the method is published in, e.g.,: Schwab S J Raymond J R Saeed M Newman G E Dennis P A Bollinger R R. *Prevention of hemodialysis fistula thrombosis. Early detection of venous stenoses. Kidney International* 1989;36:707–11.

This method has obvious disadvantages: First the empirical evaluation of the limit requiring either the acceptance of thrombosis during the evaluation period or, alternatively requiring comparison with a reference method. Further the use of a specific cannula and a specific blood flow for the measurement. This means that the treatment is influenced at least temporarily.

Another method measures the static fistula pressure. This is done with special pressure sensors positioned at the level of the fistula that are connected to the fistula either through a special cannula or through the extracorporeal circuit. Also, it is known to use the sensors already employed by the extracorporeal circuit. In this case it is necessary to correct for the height difference between the liquid level in the extracorporeal circuit and the fistula. This method too requires personnel time for the measurement of the height difference and the evaluation of the measurement. Because the patient can alter his position such a measurement can be done only once if personnel time is limited.

This method is described in: Besarab A, Al-Saghir F, Alnabhan N, Lubkowski T. Frinak S. *Simplified Measurement of Intra-Access Pressure. ASAIO Journal* 1996;42:M682–7

Stenosis can develop in the extracorporeal circuit too. These are flow resistances in cannulas that have not been taken into account correctly by the user or, alternatively, flow resistances caused by kinks in the tube, pinched tubing or by blood clotting. This stenosis may cause a reduction of the effective blood flow in the extracorporeal circuit and therefore a reduction of the efficacy or to hemolysis because of the high shear force at the point of the stenosis. To detect such stenosis pressure sensors in the extracorporeal circuit are employed that work invasively, this means they are connected through tubing or, alternatively, sensors working with special pressure transmitters. These sensors are expensive and promote blood clotting. They measure mean pressure which means that the pressure pulses in the extracorporeal circuit are smoothed by electronic hardware or software and therefore eliminated. Another patent of the inventor (DE 3806248) describes a method employing the pressure pulses for monitoring the proper function of the pressure monitor. DE 3806248 also mentions the possibility to measure the pulse frequency of the patient with this method. DE 3806248 furthermore describes a method to detect stenosis between the blood pump and the venous pressure sensor from a phase shift.

The purpose of the new invention is to describe a simple method and a device for the early detection of stenosis in the vicinity of the fistula and for continuous monitoring of the extracorporeal circuit. Additionally it is possible to measure the rotational speed of the blood pump and the pulse frequency of the patient already described previously. The method is based on the amplitude of the pressure pulses, corrected if necessary by a frequency dependent function, measured in the extracorporeal circuit with the blood pump in operation or stopped. Measurements in the clinic have shown that, with the blood pump stopped, it is possible to measure the patient's pulse downstream of the blood access in the extracorporeal circuit. It is not possible to do this with the pressure monitors of dialysis machines because these are artificially dampened as already described. Rather the observations have been made with not dampened pressure sensors. Pressure sensors of common dialysis machines are able to measure such pressure pulses too provided the electronic damping is removed.

It has been recognized surprisingly that the pulse amplitudes are higher with stenosis. Also it has been recognized that the pulses from the patient's pulse can still be recognized even with the blood pump running in case of stenosis. When the extracorporeal circuit was in operation it was not possible to find a correlation between the pressures measured before the blood pump (p(art)) and in the venous drip chamber (p(ven)) and the pressure pulses produced by the blood pump. Surprisingly it was found that an approximately linear correlation exists between the amplitude of the pressure pulses and the mean pressure if the compliance of the system is reduced by removal of the air from the system.

As already mentioned pressure monitoring in the extracorporeal system is done with systems employing partially filled pressure lines or with systems using special pressure transmitter membranes. Attempts have been made to measure the pressure directly on the tubing, this means that the tubing wall is used for pressure transmittance. This has failed with the commonly used PVC tubing because of creeping. DE 4106444 describes a method reducing the creeping effect by a mechanical bias of the tubing during storage. Surprisingly it has been found that the pressure pulses can be measured with an "acoustic contact sensor" of the company Apollo Research Corp. Denew, N.Y., USA in the frequency range of interest. This sensor has the shape of a flat cylinder that is positioned directly on the tubing which is only slightly compressed.

To limit the pressure produced by the blood pump in the extracorporeal circuit peristaltic pumps are normally so designed that the occlusion of the rollers is reduced above a typical pressure of 1–2 bar which limits the pressure. At this occasion, the fluid flows backward temporarily through the only partially occluded tube into the sucking area. If blood is pumped, it will be hemolysed by the shear forces which may result in life threatening complications. Surprisingly it has been found that this situation can be detected by an increase of the pulse amplitude as well downstream as upstream of the blood pump although the mean pressure does not increase downstream because of the flow limitation while upstream (on the sucking side) a reduction of the mean sucking pressure is measured.

The invention is now described more detailed with the help of figures and examples:

Figure 8:
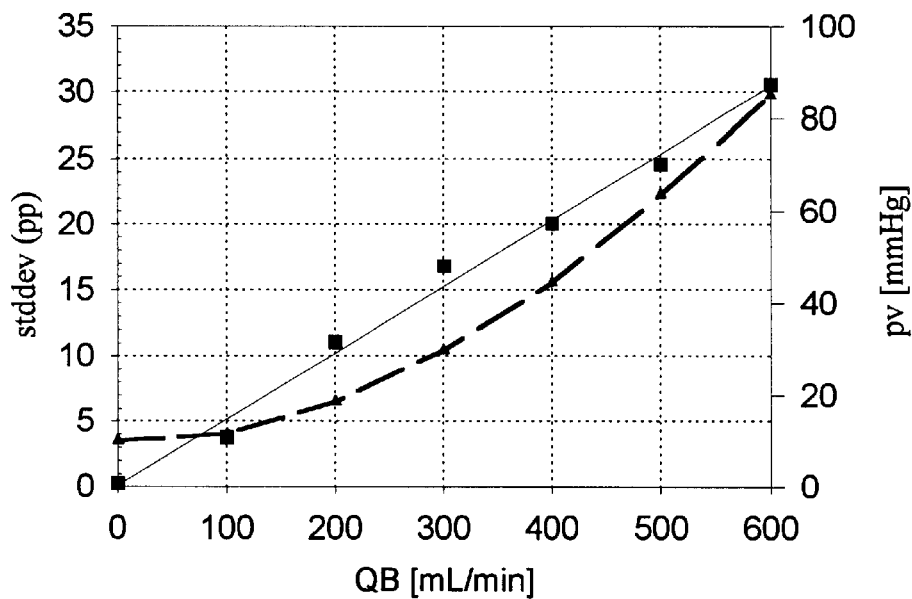
Figure 9:
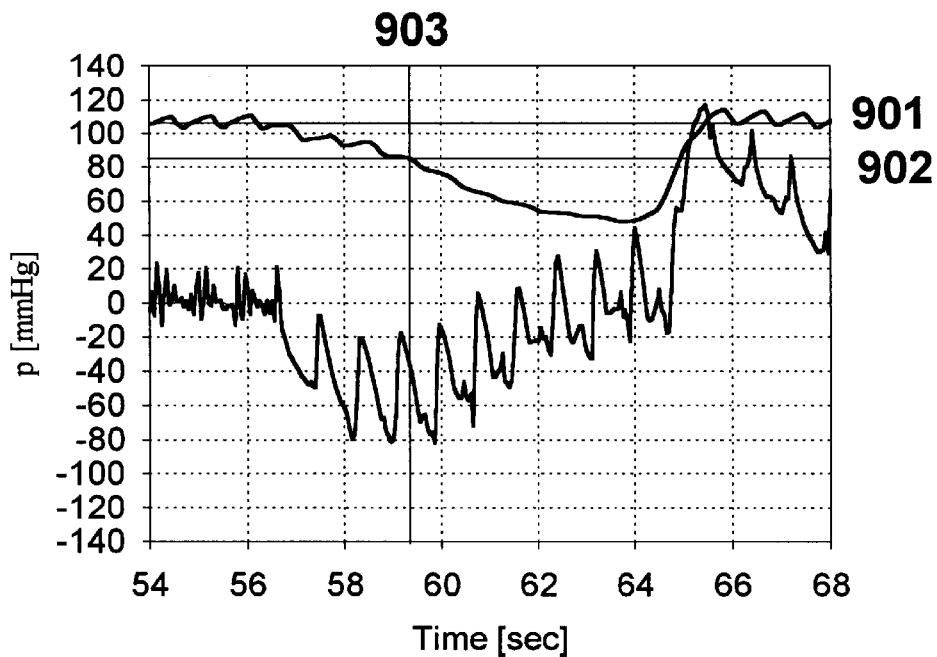

FIG. 8 shows the pressure pulse amplitude as function of the pump speed measured upstream of the blood pump FIG. 9 shows the pressure downstream of the blood pump p(pp) and at the venous measuring point p(ven) over a time period during which the cross section of the tubing between the sensors has been reduced so far that the occlusion of the blood pump has been compensated partially by the counter pressure.

Figure 10:
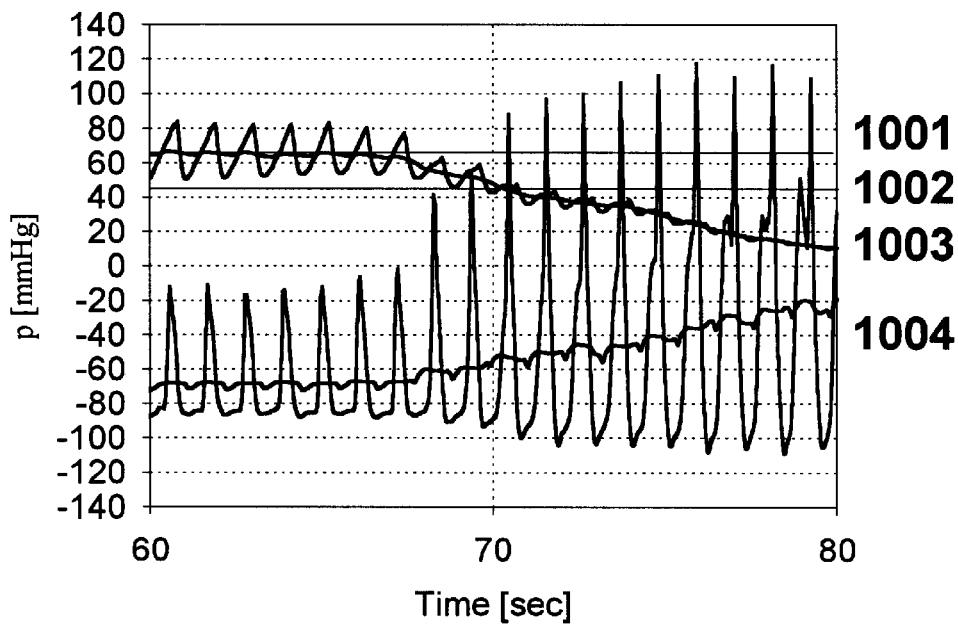

FIG. 10 shows the pressure before the blood pump p(art) and at the venous measuring point p(ven). The procedure is as described for FIG. 9.

Figure 11:
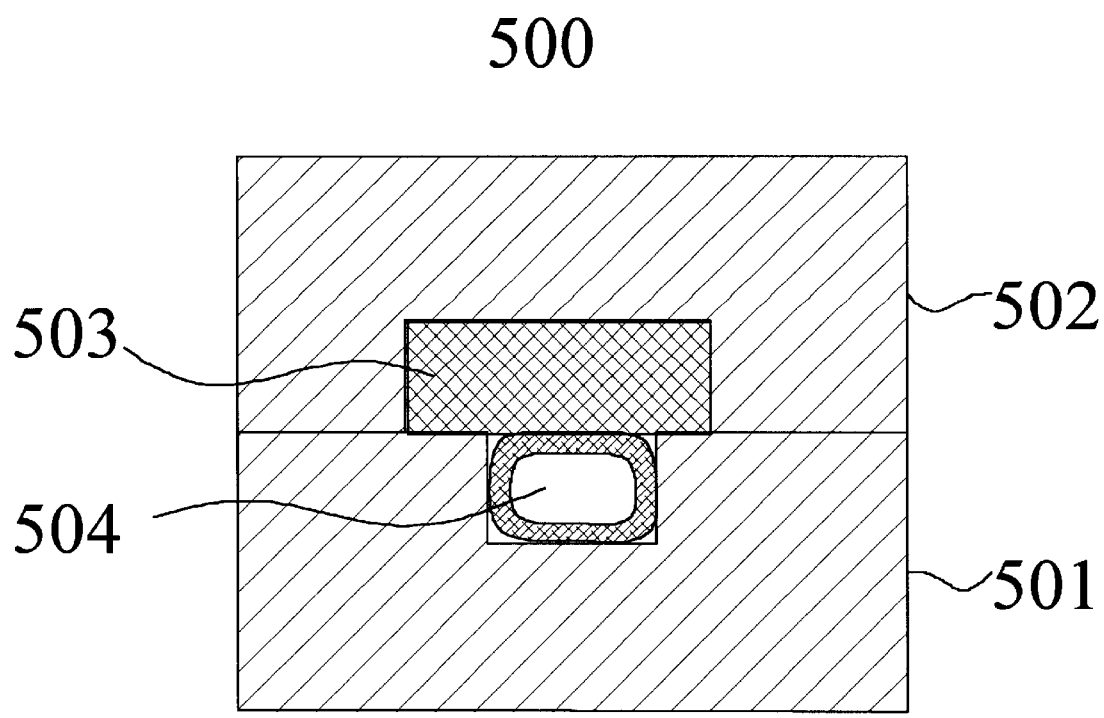

FIG. 11 shows a pressure sensor positioned directly on the tube.

Figure 1:
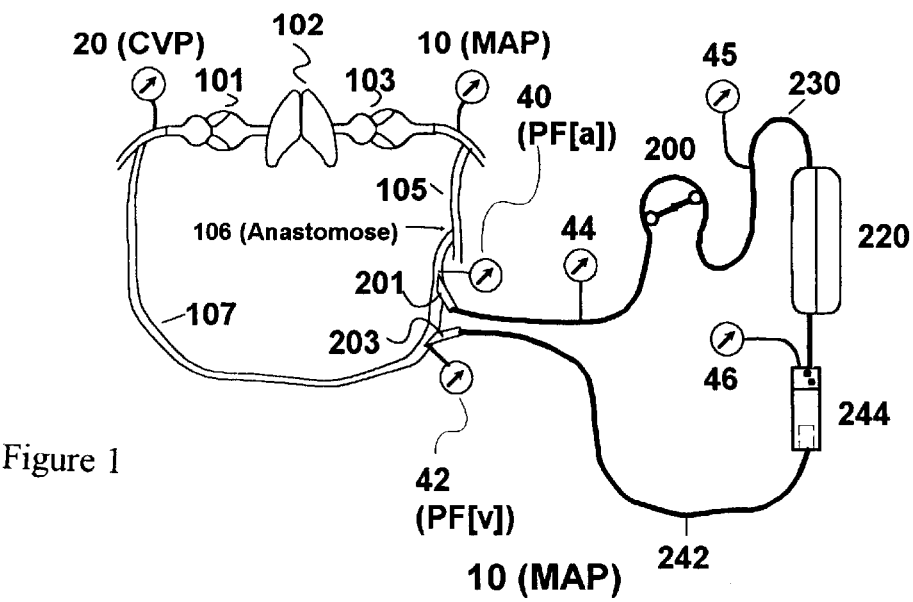
FIG. 1 shows symbolically the systemic human blood circuit with an extracorporeal circuit connected to it.

FIG. 1 shows symbolically the human systemic circuit and a connected extracorporeal circuit. Blood is pumped from the right heart 101 through the lung 102 to the left heart 103 and enters the arterial system which is at the mean arterial pressure 10 (MAP). From there, blood reaches a peripheral artery of the arm (105) connected to a peripheral vein 107 through an anastomosis 106. The said peripheral vein transports blood to the vena cava (not specifically marked) that is at the central venous pressure (CVP). From there, blood reaches the right heart which closes the systemic blood circuit. The vein is widened at the connection between artery and vein (106) by the arterial pressure and a fistula is formed that can be punctured. An arterial blood access cannula (201) is inserted into this fistula. From there, blood flows through an arterial blood tubing system (230) to a peristaltic blood pump (200) that pumps blood through the extracorporeal circuit and further to the extracorporeal treatment unit (e.g., hemodialyzer, hemofilter, hemodiafilter, plasmafilter, hemoadsorber). From the dialyzer blood returns to the systemic blood circuit through the venous tubing system 242, in which a venous drip chamber 244 is commonly integrated, and through the venous cannula 203. In the systemic circuit the pressure at the arterial puncture site is the arterial fistula pressure PF(a) 40 and at the venous puncture site it is the venous fistula pressure PF(v) 42.

In the extracorporeal circuit the pressure before the blood pump is the arterial pressure p(art) measured by the sensor 44. Downstream of the pump 200 the pressure before the dialyzer pp (post-pump arterial pressure) is often measured by an additional pressure sensor (45). In the venous blood tubing system downstream of the dialyzer 220 the venous return pressure p(ven) is measured by sensor 46, commonly connected to the venous drip chamber by a pressure measuring tube. Pressure sensors 44, 45 and 46 and the evaluation electronics connected to them are commonly designed such that the pulsations of the blood pump are smoothed. The smoothing time constant is in the range of several seconds.

Figure 2:
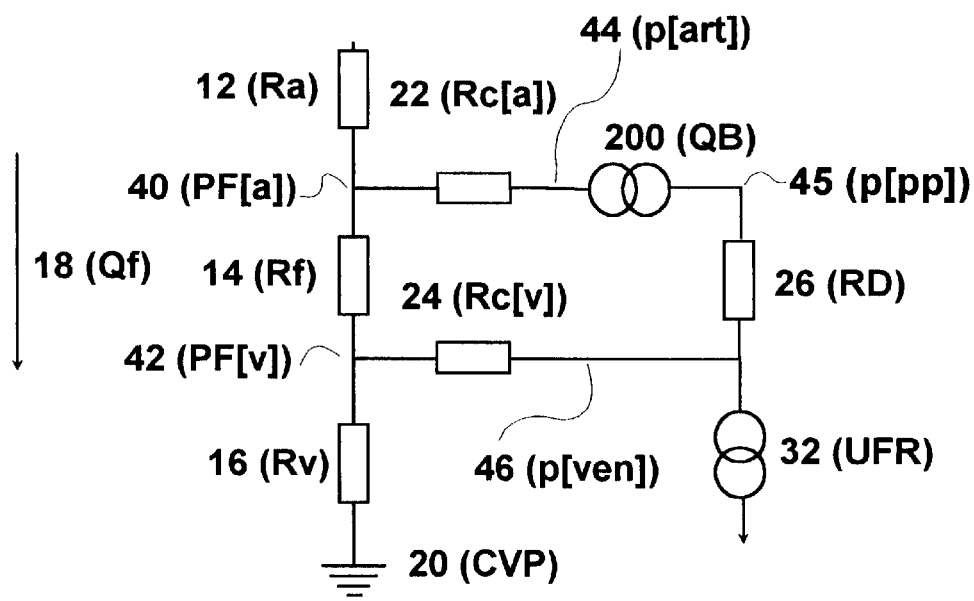
FIG. 2 shows a hydraulic circuit equivalent of the systemic and extracorporeal circuit representing flow resistances and pressures.
Figure 3:
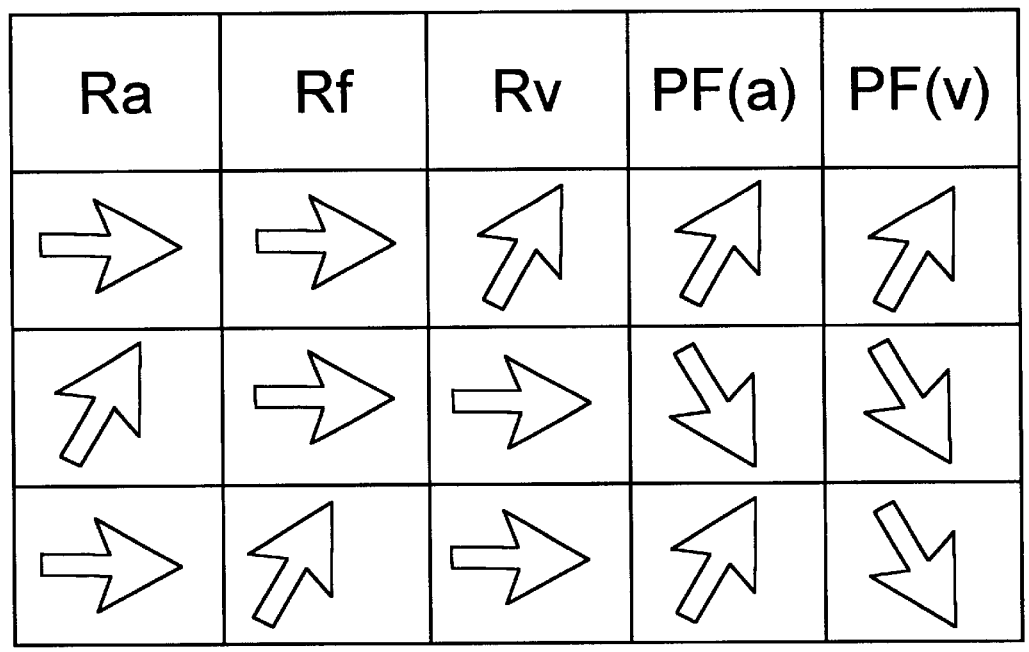
FIG. 3 shows qualitatively changes to the arterial and venous fistula pressure in case of stenosis as a function of the position of said stenosis.

FIG. 2 shows the equivalent circuit. Systemically, blood flows from the central arterial system (10) that is under mean arterial pressure (MAP) to the central venous system (20) which is under central venous pressure (CVP). The pressure drop is divided proportionally to the flow resistances Ra(12), Rf(14) and Rv(16). Ra(12) is the arterial resistance including the flow resistances of the anastomosis, Rf(14) is the resistance of the fistula between the arterial and venous blood access and Rv(16) is the venous resistance. For the case of an artificial graft between artery and vein the flow resistance of the venous anastomosis is part of this flow resistance. With the extracorporeal circuit not in use the blood flow in this circuit is Qf(18). The blood pump 200 produces the flow QB in the extracorporeal circuit. Symbolically shown is furthermore an ultrafiltration pump (32) removing a flow UFR from the dialyzer. The arterial flow resistance 22 and the venous flow resistance 24 are mostly defined by the flow resistances of the cannulas. They are approximately equal. The flow resistance of the dialyzer is symbolized by 26 (RD). Frequently, a pressure sensor pp (45) is inserted between blood pump (200) and dialyzer (220, FIG. 1) with the flow resistance RG (26), the purpose of which is to detect an increase of the flow resistance between the blood pump (200) and the venous pressure measuring point (46). An increase of the flow resistance by kinking of the tube has already caused hemolysis with fatal results in the past. The pressures in the blood access and in the extracorporeal circuit are symbolically marked with the same numbers as in FIG. 1. Ohm's law that can be applied for hydraulics allows calculation of the pressures in the circuit from the known resistances. It is discernible that the pressure Pf(v)(42) will increase if the flow resistance Rv(16) increases which is equivalent to stenosis. Stenosis can occur in the arterial and the venous part of the fistula as well as in the part between the blood accesses. From the qualitative analysis of the two pressures Pf(a)(40) and Pf(v)(42) the following conclusion can be drawn as shown graphically in FIG. 3: Stenosis in the venous segment (increase of RV) causes an increase of the arterial fistula pressure (PF(a)) as well as the venous fistula pressure (PF(v)). Arterial stenosis causes a decrease of both pressures and stenosis in the fistula causes an increase of the arterial pressure and a decrease of the venous pressure.

Stenosis (reduction of the cross section) can occur in the extracorporeal circuit as well. This too can be detected by changes of the pressures p(art), p(pp) and p(ven).

In principle, the systemic pressures PF(a)(40) and PF(v)(42) can be measured by the pressure sensors (44) and (46) in the extracorporeal circuit. It is necessary, however, to take the hydrostatic pressure differences, caused by the height differences of the fluid columns between the points of measurement and the fistula, into account. Such a measurement must be done whenever the pressure is to be evaluated. This is elaborate as already described before. For practical consideration it should be done at the beginning of dialysis but this is the time when the nursing personnel is fully occupied already.

Surprisingly it has been found by observation in the clinic that the patient's pulse can be recognized with the blood pump stopped and with pressure sensors not damped as it is common in dialysis machines. It has further become apparent that the amplitude of these pressure pulses is proportional to the mean pressure at the point of measurement. It has been recognized that the equivalent circuit is applicable for pulsating flow (comparable to alternating current) provided the time constant of the circuit is small compared to the frequency. The time constant of the circuit is the product of flow resistance and compliance of the vessels. This is equivalent to the product of resistance and capacitance R*C in the electrical analogue. A further surprising result of the measurements is that the time constant of the systemic circuit can be neglected. It has been found that the systemic pulses can be recognized in the extracorporeal circuit with the blood pump running too. Without special evaluation methods this is only possible with low pumping speeds. A special embodiment of the invention, however, describes the evaluation of the pressure course by an appropriate method, e.g., Fourier analysis allowing the separation of frequencies in order to separate the pulse frequency and amplitude from the known frequency of the blood pump.

Figure 4:
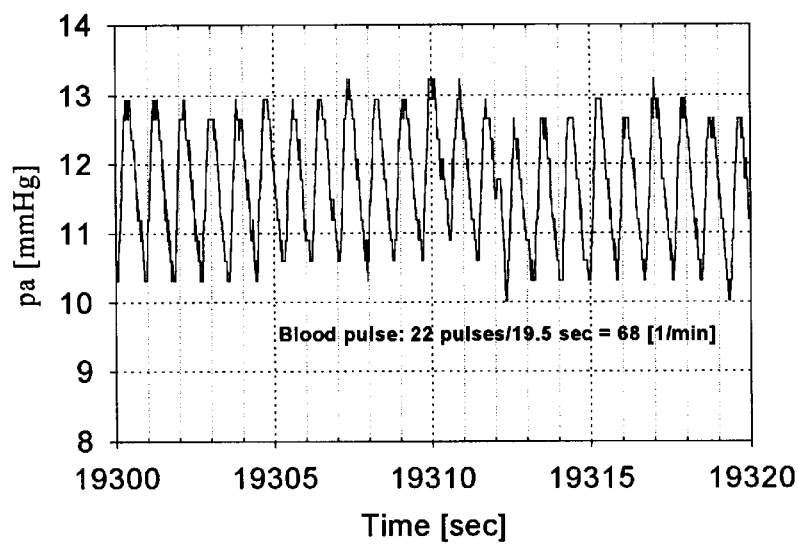
FIG. 4 shows systemic pressure pulses recorded in the arterial segment of the extracorporeal circuit with a pressure sensor with high time resolution.

FIG. 4 shows the pressure measured at sensor 44 (p(art)) without static pressure correction and measured with a time resolution of 1/20 [sec] at the end of a dialysis treatment. The fistula is "normal" with a typical fistula pressure of 25 mmHg. The pulse of the patient can be calculated from the pulses per unit time. The amplitude of the pulses is approximately 2.5 mmHg (peak-peak) at an uncorrected mean pressure of 11.7 mmHg.

Figure 5:
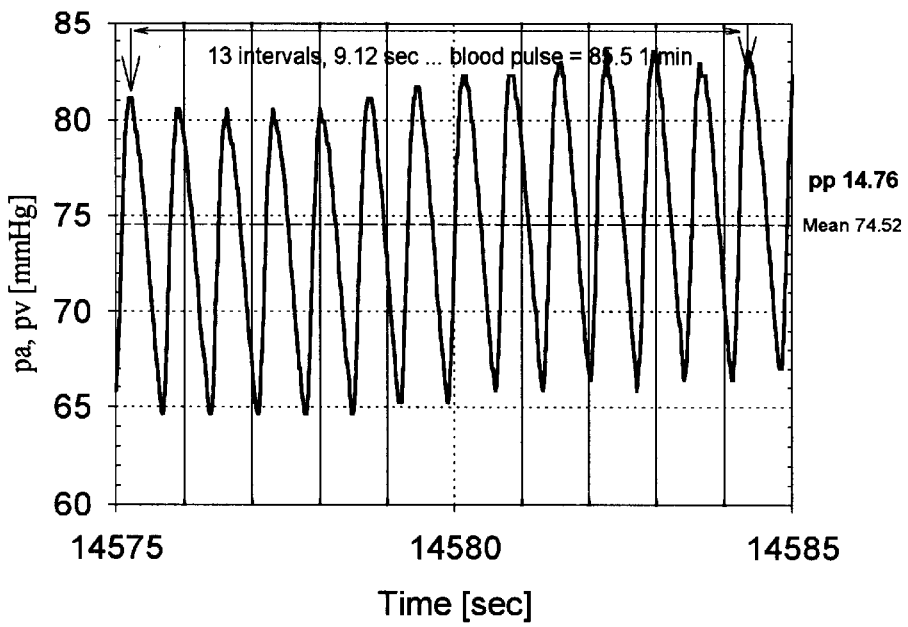
FIG. 5 shows systemic pressure pulses recorded in the arterial segment of the extracorporeal circuit with a pressure sensor with high time resolution for the case of stenosis in the fistula.

FIG. 5 shows a pressure recording, similar to FIG. 4 but measured at a fistula with stenosis between arterial and venous access and therefore with increased resistance Rf(14). It can be seen that the uncorrected mean pressure (74.5 mmHg) and the pulse amplitude (14.8 mmHg) is much higher. Again it is possible to calculate the patients' pulse form the number of pressure pulses per unit time.

Figure 6:
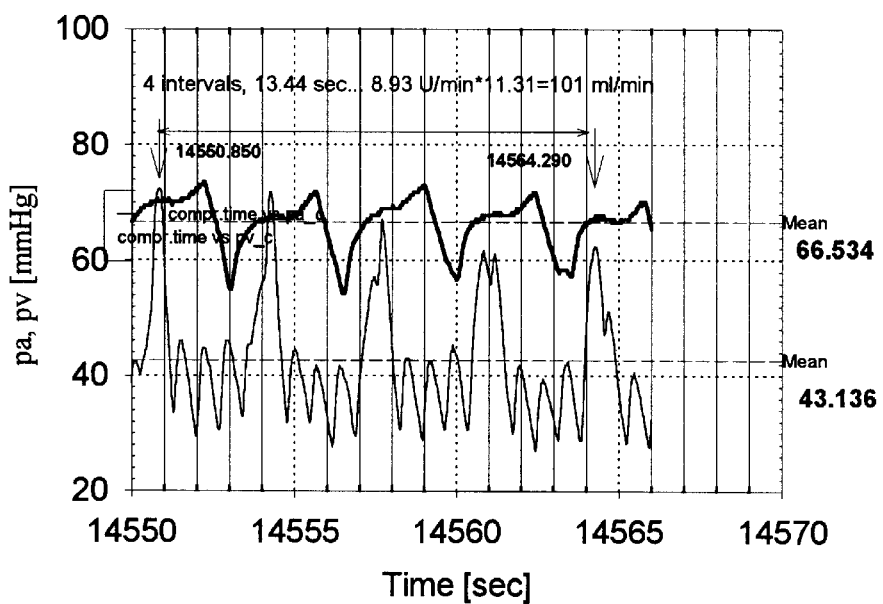
FIG. 6 shows systemic pressure pulses superimposed by pressure pulses of the blood pump

FIG. 6 shows arterial and venous pressure pulses with a blood flow of ~100 mL/min in the extracorporeal circuit. This data has been recorded immediately before the data shown in FIG. 4. The lower line is the arterial pressure pulse. The high pulses are from the blood pump and the small ones between originate from the patient's pulse. It is possible to calculate the number of revolutions per unit time from the pressure pulses per unit time produced by the blood pump. From this it is possible to calculate the pump rate with the help of a geometry constant. For a peristaltic blood pump, the number of pulses per revolution is defined by the number of rollers. With n(2) rollers there are n(2) pulses per revolution.

The upper curve of FIG. 6 shows the pressure recording at sensor 46 (p(ven)). It is possible to calculate the blood pump rate from these as well. Furthermore it can be seen that these pulses are phase shifted compared to the arterial pulses. Systemic pressure pulses from the patient cannot be recognized. This is caused by the compliance of the partially filled drip chamber (244) causing strong damping and because of the small venous pulses at point 42 (PF(v)) caused by the increased flow resistance 14 (Rf) in this patient.

Figure 7:
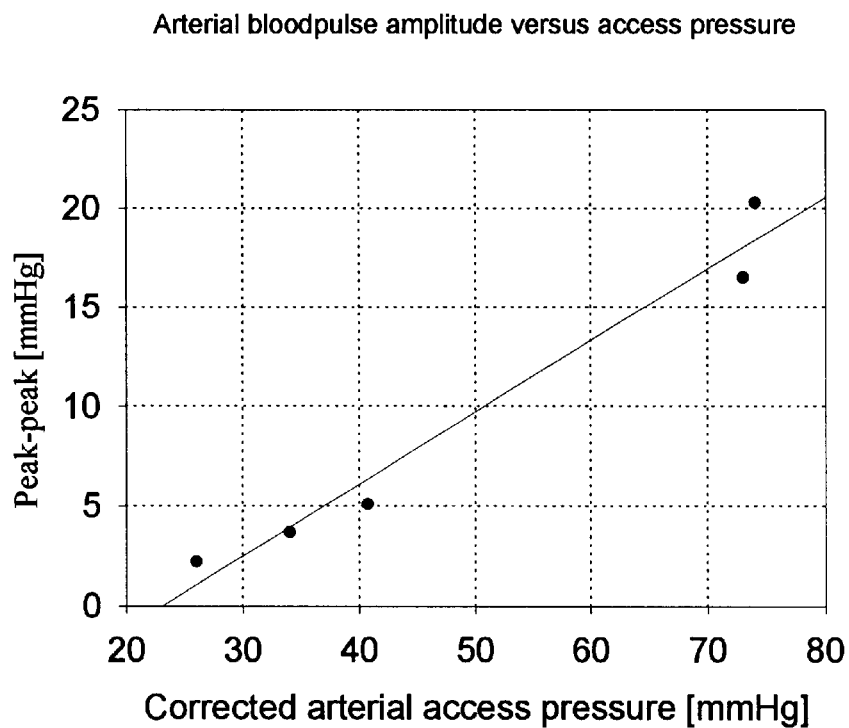
FIG. 7 shows the correlation between the smoothed arterial fistula pressure and the pulse amplitude measured at the same position in several patients.

FIG. 7 shows the evaluation of the pressure pulses of several patients. Shown is the amplitude (peak-peak) of the pressure pulses measured with sensor 44 (p(art)) in the extracorporeal circuit with the blood pump 200 stopped versus the arterial fistula pressure PF(a)(40) corrected for static influences. There is good linearity as can be seen.

FIG. 8 shows the mean pressure measured at 46 (p(ven)), triangles, dashed line) and the standard deviation of the pressure pulses measured at 44 (p(art), squares, full line). The arterial pressure pulses (46) were measured with a pressure transducer in direct contact with the tube (FIG. 11) to avoid any compliance from pressure measuring lines. Compliance causes strong, frequency depending damping. The pressure 46 (p(ven)) is shown for comparison.

FIG. 9 shows the time course of the pressure over time measured at point 46 (p[ven]), upper curve) and at point 45 (p[pp]) downstream of the blood pump (lower curve).

Furthermore, horizontal lines 901 show the mean venous pressure (46, p[ven]) and a fictive alarm limit (902) 20 mmHg below. With a common dialysis machine an alarm would be triggered when the pressure falls below this alarm limit. This would be the case at time 903. The test was performed with water at 37° C. and the extracorporeal circuit shown by FIG. 1. The patient was replaced by a thermostated vessel. The dialyzer was replaced by a short circuit connection. Cannulas 16 g/25 mm were used. The flow was 400 mL/min.

For recording this curve the blood tube was slowly clamped downstream of the pump and the sensor 45 (p[pp]) causing an increase of the mean pressure downstream of the pump followed by a temporary reduction of the occlusion and a reduction of the pump flow. Already a reduction of the occlusion for a short time causes a distinct increase of the pressure pulses measured at 45 before the reduction of the flow causes a fall of the venous pressure to the value 902. Measurement of pressure pulses downstream of the blood pump therefore allows the sensitive detection of the occlusion limit at which hemolysis of blood occurs. The common venous pressure would only trigger an alarm at a pressure drop of approx. 10%. At this point 10% of the blood flow would be hemolysed. The experiment of FIG. 9 shows a quick-motion of the events that may occur in the praxis. In the praxis it is possible that the extracorporeal circuit is operated with partial occlusion over a longer period. Even when an alarm is triggered the most likely reaction of the personnel is to change the alarm limits because the venous pressure monitor does not indicate a clearly dangerous situation. The present invention allows the unmistakable indication of the dangerous situation.

FIG. 10 shows a further test done with the test setup described for FIG. 9 but with the blood pump operated at 300 mL/min. The figure includes again horizontal lines 1001 and 1002 for the venous mean pressure at the beginning and the fictive limit below. Furthermore the venous pressure (p[ven], 46) measured with high time resolution and averaged (upper curve, 1003) and the arterial pressure p[art], 44 measured with high time resolution and averaged (1004) and with a conventional pressure transducer connected through an air-filled line. As can be seen the pressure pulse amplitude increases sharply on the arterial side with reduced occlusion. The mean pressure is reduced absolutely (less negative) because of the reduction of the mean flow. It is therefore possible to detect the hazardous situation described for FIG. 9 with a conventional sensor arrangement by monitoring the quotient of pressure pulse amplitude and mean pressure that can be described for normal operation by a constant (resistance of the cannula, compliance of the pressure measuring line, frequency of the pump). Alternatively the pressure pulse amplitude can be monitored for larger deviations (>50%) at constant blood flow.

FIG. 11 shows the measuring setup with the sensor measuring the pressure pulses directly on the tube. 500 is the mounting for the sensor 503. This mounting can be dismantled into two parts 501 and 502 to allow insertion of the tube 504. The tube 504 is slightly deformed allowing mechanical contact to the sensor 503. For the experiment described, the tubing diameter of 6 mm nominal, has been reduced by 1 mm in the direction of the contact force. The sensor is electrically connected to an evaluation unit not shown in detail. Such evaluation units are available on the market.

Measurement of pressure pulses can be performed with pressure sensors integrated into dialysis machines. Furthermore with pressure sensors independent of the dialysis machine connected to the extracorporeal circuit either through a partially air-filled tube or with a membrane. Measurement with the sensor in direct contact with the tube as described in this invention is preferred. The evaluation of the pressure pulses can be done by evaluating the pulse amplitude (peak-peak) but it is also possible to average the result over a predetermined time interval (e.g., 3 sec) to allow for the discrimination of patient movements. A preferred method is the calculation of the standard deviation over a predetermined interval (e.g., 3 sec), because simple software routines are available for this. Of course, the use of other algorithms is possible that produce a measure for the pulse oscillations. Also, it is possible to amplify special frequencies or frequency ranges to increase the sensitivity or, more general to apply a filter function.

As already mentioned initially the method described by this invention is applicable for all extracorporeal treatment devices. Instead of cannulas catheters can be used. Instead of dialyzers the appropriate treatment units, e.g., hemoperfusion cartridges, oxygenators, heat exchanger, cartridges for irradiation with electromagnetic radiation or for the treatment with electromagnetic fields can be used. In case several of these devices are used in series an additional sensor can be used between the treatment units. The detection of stenosis in a blood access produced by a shunt between an artery and a vein (graft, fistula) can be improved by the use of the systemic blood pressure. As can be seen from the equivalent circuit of FIG. 2 the calculation of the relative resistances is possible from the ratio of the total pressure drop (MAP-CVP) and the pressure measured at the blood access (PF(v), PF(a)). The central venous pressure can be neglected and it is possible to calculate the ratio of PF/MAP. The mean arterial pressure is a function of the systolic and diastolic pressure. Nevertheless it may be advantageous to normalize with the difference between systolic and diastolic pressure rather than with the MAP. The limit from which stenosis is concluded in a certain area depend on the type of blood access. With grafts a normal value of 53% of the mean arterial pressure (MAP) is published (Besarab A, Frinak S. The prevention of access failure: pressure monitoring . . . ASAIO Journal 1998; 44: 35–7). For the evaluation of the pressure pulses this corresponds to the pulse amplitude normalized by the difference of systemic and diastolic blood pressure. The mathematical relationships between MAP, systolic and diastolic pressures and between pulse amplitudes and standard deviations are known allowing a conversion at any time.

Eventually, the limit values have to be established in the clinical praxis.

An evaluation unit according to the invention will at least show the pulse amplitude of a pressure. Because data about the systemic blood pressure is available, the normalized pressure can be calculated and displayed in a further embodiment of the invention. Eventually limits may be adjustable and warnings may be displayed when these limits are exceeded.

In summary the described invention allows the detection of stenosis in extracorporeal blood treatment without additional, expensive hardware or with simplified hardware respectively that has not been possible or only with considerably higher expense until now. This can increase the safety and reliability of extracorporeal blood treatment.

What is claimed is:

1. An apparatus for detecting stenosis in a blood circuit which is part of an extracorporeal blood treatment system for a patient, the blood circuit comprising an extracorporeal portion and a patient portion, the extracorporeal portion being connected hydraulically to the patient portion with a blood access device, the apparatus comprising:

a. a pressure pulse source in the blood circuit creating pressure pulses;

b. at least one pressure sensor in the blood circuit; and c. an evaluation unit receiving a measured pressure pulse amplitude proportional signal transmitted by the pressure sensor, said evaluation unit detecting stenosis using a deviation from a predetermined value of the pressure pulse amplitude proportional signal received from the pressure sensor.

2. The apparatus of claim 1, wherein the pressure pulse source is a pulsating blood pump in the extracorporeal portion of the blood circuit.

3. The apparatus of claim 2, wherein the pulsating blood pump is a peristaltic blood pump.

4. The apparatus of claim 1, wherein the pressure sensor is positioned between the blood access and the pressure pulse source.

5. The apparatus of claim 1, further comprising an extracorporeal blood treatment device hydraulically completing the extracorporeal portion of the blood circuit.

6. The apparatus of claim 5, wherein the pressure sensor is positioned between the pressure pulse source and the extracorporeal treatment device.

7. The apparatus of claim 5, wherein the pressure sensor is positioned between the extracorporeal treatment device and the blood access.

8. The apparatus of claim 5, wherein the extracorporeal blood treatment device is selected from the group consisting of hemodialyzer, hemofilter, hemodiafilter, plasmafilter, and hemoadsorber.

9. The apparatus of claim 5, wherein the pressure sensor is built into the extracorporeal blood treatment device.

10. The apparatus of claim 1, wherein the pressure pulse amplitude proportional signal is corrected by a pulse frequency dependent function.

11. The apparatus of claim 1, wherein the pressure pulse amplitude proportional signal is calculated from the peak-to-peak amplitude.

12. The apparatus of claim 1, wherein the pressure pulse amplitude proportional signal is calculated from a standard deviation computed over a predetermined interval.

13. The apparatus of claim 1, wherein the pressure pulse amplitude proportional signal is corrected by blood pump rate.

14. An apparatus for detecting stenosis in an arterial-venous shunt used as a blood access in an extracorporeal treatment for a patient, the device comprising:

a. at least one blood access cannula;

b. an extracorporeal blood circuit hydraulically connected to the blood access cannula;

c. an evaluation unit;

d. at least one pressure sensor in the extracorporeal blood circuit and sending a signal to the evaluation unit, wherein a stenosis in the arterial-venous shunt is detected from a deviation of a pressure pulse amplitude proportional signal measured by the pressure sensor from a predetermined value; and e. a pressure pulse source in the blood circuit creating pressure pulses.

15. The apparatus of claim 14, wherein the pressure pulse amplitude proportional signal is normalized by a mean arterial pressure.

16. The apparatus of claim 14, wherein the pressure pulse amplitude proportional signals is normalized with a difference between a systolic blood pressure and a diastolic blood pressure.

17. The apparatus of claim 14, further comprising an extracorporeal treatment device.

18. The apparatus of claim 17 in which one of the at least one pressure sensor is built into the extracorporeal treatment device.

19. The apparatus of claim 17, wherein the extracorporeal treatment device is selected from the group consisting of hemodialyzer, hemofilter, hemodiafilter, plasmafilter, and hemoadsorber.

20. An apparatus for detecting a loss of occlusion in a peristaltic pump, comprising:

a. a pressure pulse source in a blood circuit;

b. an evaluation unit; and c. at least one pressure sensor in the blood circuit and transmitting a signal to the evaluation unit, wherein the loss occlusion is detected from an increase of a pressure pulse amplitude signal from a predetermined value.

21. The apparatus of claim 20, wherein the pressure pulse amplitude signal is normalized by a mean pressure measured with the same pressure sensor.

22. The apparatus of claim 20, further comprising an extracorporeal treatment device.

23. The apparatus of claim 22 in which one of the at least one pressure sensor is built into the extracorporeal treatment device.

24. The apparatus of claim 22, wherein the extracorporeal treatment device is selected from the group consisting of hemodialyzer, hemofilter, hemodiafilter, plasmafilter, and hemoadsorber.

25. An apparatus for monitoring a hydraulic tubing in a blood circuit, comprising:

a. a source for creating pressure pulses in the blood circuit; and b. a pressure sensor for measuring the pressure pulses, whereby the pressure sensor is mechanically coupled directly to an outer wall of the tubing.

26. An apparatus for detecting stenosis in a blood circuit which is part of an extracorporeal blood treatment system for a patient, the blood circuit comprising an extracorporeal portion and a patient portion, the extracorporeal portion being connected hydraulically to the patient portion with a blood access device, the apparatus comprising:

a. at least one pressure sensor hydraulically connected to the blood circuit;

b. an evaluation unit receiving a measured pressure pulse amplitude proportional signal transmitted by the pressure sensor, said evaluation unit detecting stenosis using a deviation from a predetermined value of the pressure pulse amplitude proportional signal received from the pressure sensor; and c. a pressure pulse source in the blood circuit creating pressure pulses.

* * * * *